United States Patent
Nagasaki et al.

[11] Patent Number: 6,144,446
[45] Date of Patent: Nov. 7, 2000

[54] METHOD AND APPARATUS FOR INSPECTING FOREIGN SUBSTANCE

[75] Inventors: Tatsuo Nagasaki; Ken Shimono, both of Hirakata, Japan

[73] Assignee: Matsushita Electric Industrial Co., Ltd., Osaka-fu, Japan

[21] Appl. No.: 08/980,817

[22] Filed: Dec. 1, 1997

[30] Foreign Application Priority Data

Nov. 29, 1996 [JP] Japan .................................. 8-319838

[51] Int. Cl.$^7$ .................................................. G01N 21/94
[52] U.S. Cl. ...................................... 356/237.3; 356/239.8
[58] Field of Search .............................. 356/237.3, 237.4, 356/239.8

[56] References Cited

U.S. PATENT DOCUMENTS 5,017,798  5/1991  Murakami et al. ...................... 356/431
5,712,701  1/1998  Clementi ................................. 356/343

FOREIGN PATENT DOCUMENTS 63-186132   8/1988   Japan .
63-241343  10/1988   Japan .
3-72248     3/1991   Japan .

*Primary Examiner*—Richard A. Rosenberger
*Attorney, Agent, or Firm*—Wenderoth, Lind & Ponack, L.L.P.

[57] ABSTRACT

An inspecting method for inspecting foreign substances, comprising projecting beams from an illumination system arranged above a light-permeable body to be inspected with an angle of incidence of a first elevation angle onto an upper face of the body, and receiving a reflecting light and a scattering light generated by the beams with a photodetecting angle of a second elevation angle by a photodetecting system. The method further comprising, before the beams are projected, setting a width of the beams of the illumination system to be not larger than w calculated according to an expression $w < 2 \cdot \sin \alpha \cdot t \{\tan[\sin^{-1}\{\sin(90°-\alpha)/n\}] - \tan[\sin^{-1}\{\sin(\theta-90°)/n\}]\}$ from the angle of incidence $\alpha$, the photodetecting angle $\theta$, a thickness $t$ of the body and a refractive index $n$ of the body to a substance over the body.

8 Claims, 6 Drawing Sheets

METHOD AND APPARATUS FOR INSPECTING FOREIGN SUBSTANCE

BACKGROUND OF THE INVENTION

The present invention relates to a method and an apparatus for inspecting foreign substances, such as dust, human hairs, human skin, metallic elements, glass, chipping, process products, etc., which are adhered to front faces of light-permeable bodies to be inspected, such as for example, glass plates used in liquid crystal panels, base boards of optical disks and hard disks, CCD sealing plates, surface acoustic wave (SAW) filters of electronic parts, etc. More specifically, the present invention relates to a method and an apparatus whereby only foreign substances adhering to front faces of the inspection bodies are distinguished and detected from those adhering to rear faces of the inspection bodies.

A liquid crystal panel has fine liquid crystal pixel electrodes and thin film transistors formed on a front face of a glass plate. The quality of the liquid crystal panel as a product is greatly adversely influenced if a foreign substance adheres to the front face of the glass plate. Inspection by an inspecting apparatus is thus necessary to inspect foreign substances adhering to the front face. Meanwhile, the glass substrate used in the liquid crystal panel is an almost transparent thin plate having a thickness of approximately 1 mm and a high light-permeability, which potentially leads to a problem in that not only will foreign substance adhering to the front face (referred to as a "front foreign substance"), be detected but the foreign substance adhering to a rear face (referred to as a "rear foreign substance") of the substrate will also be detected. The glass substrate is assembled into the liquid crystal panel generally in a state with the rear face fixed at the side to observe displayed images or to pass a back light. The rear face is accordingly enough to be a simple glass face and the adhesion of the foreign substance to the rear face does not matter at all so long as the adhering substance is very small. It is so adapted in many cases as not to recognize the rear foreign substance as a defect. If the rear foreign substance was detected to be a defect, even a good liquid crystal panel would be determined to be defective, thereby lowering a yield and causing a large loss of products.

In the meantime, the glass plates are recently required to be light-weight in accordance with an increasing need for light-weight liquid crystal panels, and consequently the thickness of the glass substrates is decreased from approximately from 1 mm to 0.7 mm.

Under the circumstances, the above-discussed wrong detection of the rear foreign substance draws more and more attention.

In order to detect only the front foreign substance of a light-permeable body to be inspected, e.g., glass substrate of the liquid crystal panel without detecting the rear foreign substance, various methods are carried out:

1. Light projected from each of two light sources are irradiated to the body to be inspected, resultant scattering light is detected by corresponding photodetectors, and intensities of the scattering light is compared, thereby to detect the foreign substance (Unexamined Japanese Laid-Open Patent Publication No. 63-186132).

2. A plurality of photodetecting means are arranged. Light is cast from each direction to the body to be detected and scattering light on the body is compared at the detectors, thereby to detect the foreign substance (Unexamined Japanese Laid-Open Patent Publication No. 63-241343).

The constitution in the above methods is complicated due to a requirement of installing a plurality of light sources and photodetectors.

On the other hand, there is a method of a simple constitution as follows.

3. An angle held between an angle of incidence and a photodetecting angle to the body to be inspected is set to be 90°, and a light slit plate is arranged immediately before a photodetector. Only a scattering light generated by the foreign substance is guided to the photodetector, thereby to detect the foreign substance (Unexamined Japanese Laid-Open Patent Publication No. 3-72248). A technique of the method will be described with reference to FIG. 6, specifically with only the use of optical paths for the sake of brevity. A laser illumination A is generated from a laser 24 assuming an angle of incidence of 2° to a glass 22 which is a body to be inspected, thereby forming an image focused on a front face of the glass 22. The front face of the glass 22 is thus illuminated by the laser illumination of a reduced size. A photodetecting angle of a photodetector 26 consisting of a photomultiplier is set to be 88° so that an angle held between the photodetecting angle and the incidence of angle of the laser illumination is 90°. A slit 25 is placed in front of the photodetector 26. The slit 25 is formed to correspond to an image formation position on an optical path 31a of a reflecting light or scattering light generated from a foreign substance 23a adhering to a front face part of the glass 22. In the constitution, the reflecting light or scattering light generated from the foreign substance 23a adhering to the front face of the glass 22 reaches the photodetector 26 through the optical path 31a and it is detected as the foreign substance. In contrast, a reflecting light or scattering light generated from a foreign substance 23b adhering to a rear face of the glass 22 illuminated by the laser illumination through the glass 22 runs an optical path 31b and is shut by the slit 25. Therefore, the reflecting light or scattering light from the rear foreign substance 23b does not reach the photodetector 26 and is not detected as the foreign substance.

It is difficult, however, in the above method to distinguish the front foreign substance 23a from the rear one 23b. In other words, the rear foreign substance is practically sometimes detected in the method. The reason for this will be described with reference to FIG. 7. The laser illumination A in FIG. 6 is illustrated ideally to trace a single optical path, but is actually composed of beams of a width W. Since the laser illumination A generated from the laser 24 is reduced to be focused on the front face of the glass 22, the beams of the laser illumination A can be regarded to be parallel in the vicinity of the glass 22. The parallel beams in the vicinity of the glass 22 have the width W in a vertical direction. A lower end of the beams touches the front face of the inspection substrate 22 along a route $P_1Q_1$, and reaches the rear face in a route $Q_1R_1$ after being refracted at the front face. An upper end of the beams comes to the front face of the substrate 22 in a route $P_2Q_2$ and is then refracted to reach the rear face in a route $Q_2R_2$. If a foreign substance is present in a range $R_1$–$R_2$ of the rear face of the substrate 22, the beams hit the foreign substance thereby to be scattered or reflected. On the other hand, considering a route for the scattering or reflecting light from the foreign substance present at the rear face of the substrate 22 to enter the photodetector 26 through the slit 25, a part of the light generated from the foreign substance at a position S in FIG. 7 comes to the front face of the substrate 22 along a route $SQ_0$, is refracted and enters the photodetector 26 through the slit 25. Therefore, as is clear from FIG. 7, in the event that the beam width W is larger than a predetermined value and the beams fall in the range $R_1$–$R_2$ of the rear face when the foreign substance exists at a specific position in the range (in this case, position S), the illumination light is scattered or reflected, and a part of the light passes through the slit 25 to reach the photodetector 26. The foreign substance is eventually detected although the foreign substance is at the rear face of the substrate 22.

As is discussed hereinabove, conventionally, a plurality of photodetectors or the like arrangement is required to detect the foreign substance adhering to the front face of the light-permeable body to be inspected, resulting in the complicated constitution, while the simple constitution cannot fully distinguish foreign substances at the front and rear faces of the body to be inspected.

SUMMARY OF THE INVENTION

The present invention has for its object to provide a method and an apparatus whereby only foreign substances adhering to a front face of a light-permeable body to be inspected can be surely detected in a simple constitution.

In accomplishing these and other aspects, according to a first aspect of the present invention, there is provided an inspecting method for inspecting foreign substances, which comprises: projecting beams from an illumination system arranged above a light-permeable body to be inspected with an angle of incidence of a first elevation angle onto an upper face of the body; and receiving a reflecting light and a scattering light generated by the beams with a photodetecting angle of a second elevation angle by a photodetecting system. The method further comprising, before the beams are projected, setting a width of the beams of the illumination system to be not larger than w calculated according to an expression $$w<2*\sin\alpha*t\{\tan[\sin^{-1}\{\sin(90°-\alpha)/n\}]-\tan[\sin^{-1}\{\sin(\theta-90°)n\}]\}$$

from the angle of incidence α, the photodetecting angle θ, a thickness t of the body and a refractive index n of the body to a substance over the body.

According to a second aspect of the present invention, there is provided a foreign substance inspecting method according to the first aspect, wherein a light source of the illumination system is a laser light source and the beam width of the illumination system is a half bandwidth at a focal plane of the body.

According to a third aspect of the present invention, there is provided a foreign substance inspecting method according to the first aspect, wherein the body is a liquid crystal panel.

According to a fourth aspect of the present invention, there is provided a foreign substance inspecting method according to the first aspect, wherein the body is a base board of an optical storage medium.

According to a fifth aspect of the present invention, there is provided an inspecting apparatus for inspecting foreign substances, which comprises: an illumination system arranged above a light-permeable body to be inspected for projecting beams with an angle of incidence of a first elevation angle onto an upper face of the body; a photodetecting system for detecting a reflecting light and a scattering light generated by the beams with a photodetecting angle of a second elevation angle; and a setting unit for setting a width of the beams of the illumination system to be w calculated according to an expression $$w<2*\sin\alpha*t\{\tan[\sin^{-1}\{\sin(90°-\alpha)/n\}]-\tan[\sin^{-1}\{\sin(\theta-90°)n\}]\}$$

from the angle of incidence α, the photodetecting angle θ, a thickness t of the body and a refractive index n of the body to a substance over the body.

According to a sixth aspect of the present invention, there is provided a foreign substance inspecting apparatus according to the fifth aspect, wherein a light source of the illumination system is a laser light source and the beam width of the illumination system is a half bandwidth at a focal plane of the body.

According to a seventh aspect of the present invention, there is provided a foreign substance inspecting apparatus according to the fifth aspect, wherein the body is a liquid crystal panel.

According to an eighth aspect of the present invention, there is provided a foreign substance inspecting apparatus according to the fifth aspect, wherein the body is a base board of an optical storage medium.

The method and apparatus provided according to the present invention enable a sure detection of only foreign substances adhering to the front face of the light-permeable body to be inspected in the simple constitution.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE PREFERRED EMBODIMENT

Figure 1:
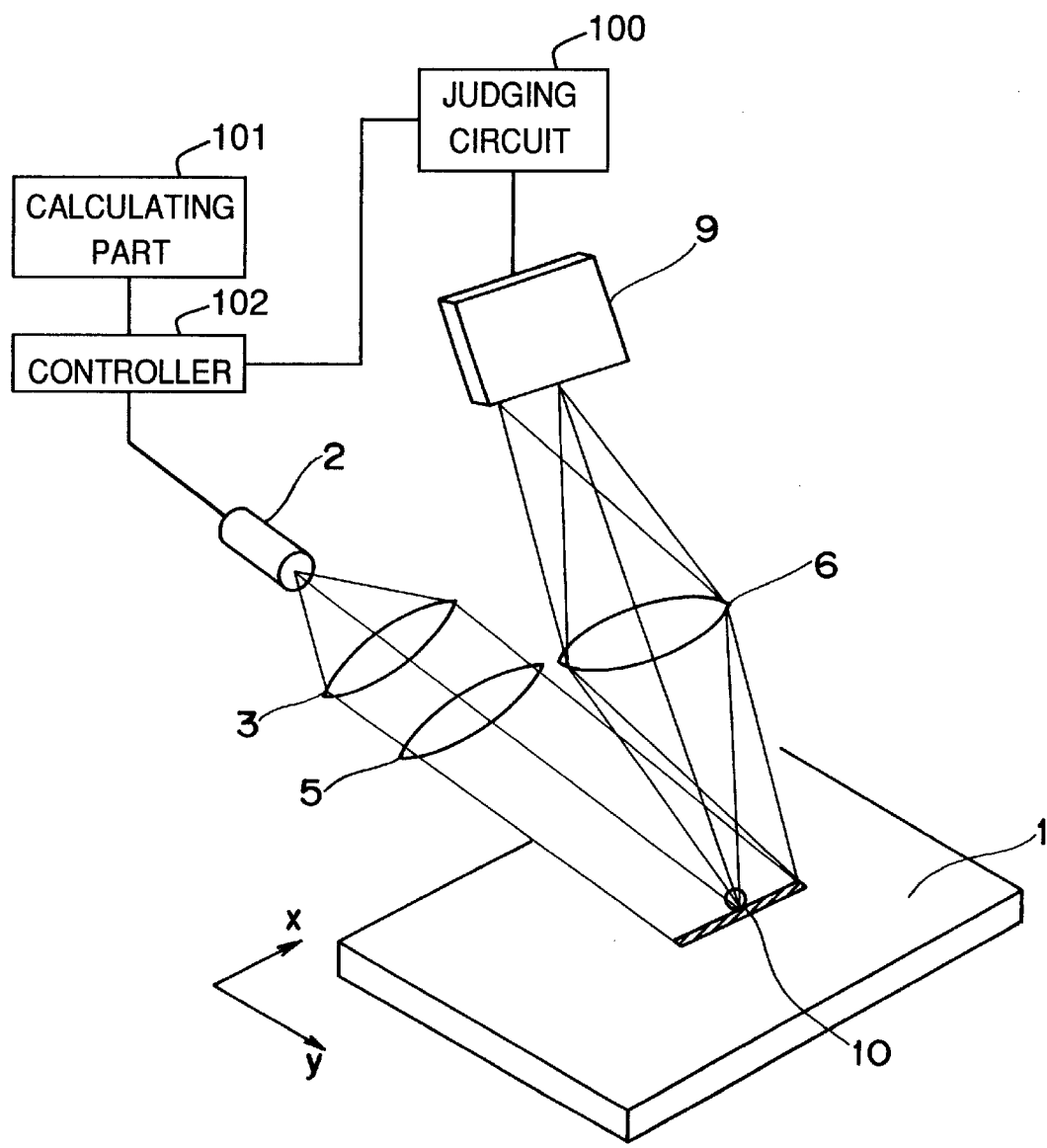
FIG. 1 is a diagram schematically showing the constitution of a foreign substance inspecting apparatus according to a first embodiment of the present invention.

Before the description of the present invention proceeds, it is to be noted that like parts are designated by like reference numerals throughout the accompanying drawings.

The present invention will be described with reference to FIGS. 1–5 and 8 taken in conjunction with one preferred embodiment thereof.

Figure 2:
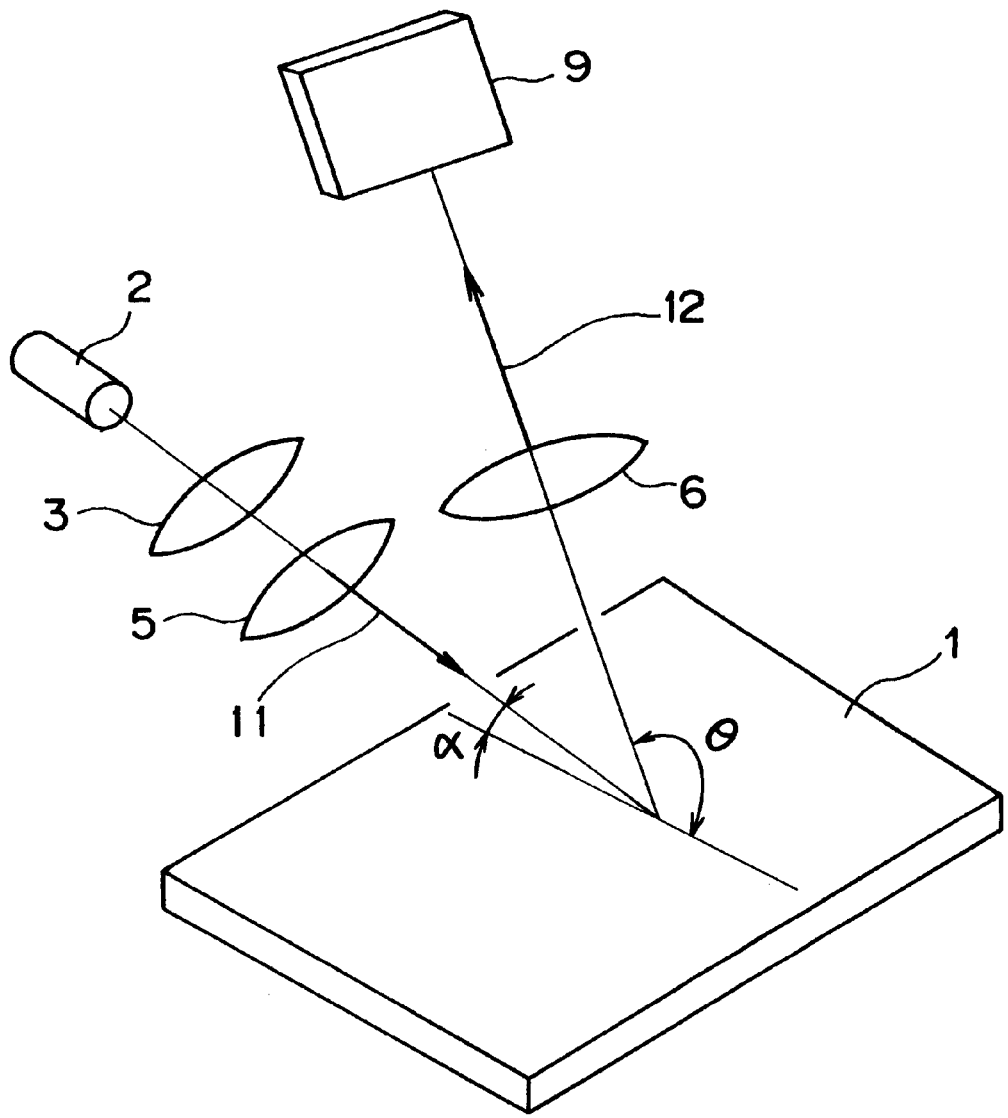
FIG. 2 is a vectorial explanatory diagram of the first embodiment.

FIG. 1 is a diagram of the basic constitution of a foreign substance inspecting method and a foreign substance inspecting apparatus according to a first embodiment of the present invention. FIG. 2 is a diagram of angles and vectors developed from FIG. 1 for the purpose of description, in which the same reference numerals represent the same parts as in FIG. 1. In FIG. 1, an illumination system of an example is constructed by a laser light source 2, a collimator lens 3 for turning light from the laser light source into parallel beams, and a cylindrical lens 5 having a focal plane at a front face of a light-permeable substrate 1 to be inspected (referred to as an "inspection substrate") and forming an image of a line from the parallel beams. The focal plane of the cylindrical lens 5 coincides with a focal plane at the front side of an objective lens 6. A line sensor 9 is arranged on an image formation face of the objective lens 6. These members 6, 9 constitute an example of a photodetecting system. The line sensor 9 is connected to a known judging circuit 100. The inspection substrate 1 is placed on a known movable table (not shown) and inspected all over the surface in a y main scanning direction and an x sub scanning direction.

In FIG. 2, a vector 11 in an incident direction indicates an optical axis of the illumination system consisting of the laser source 2, collimator lens 3, and cylindrical lens 5, which assumes an angle of incidence $\alpha$ to the inspection substrate 1. A vector 12 in a photodetecting direction shows an optical axis of the photodetecting system comprising the objective lens 6 and line sensor 9, assuming a photodetecting angle $\theta$ to the inspection substrate 1. For instance, the angle of incidence $\alpha$ and the photodetecting angle $\theta$ are respectively set to be approximately 2° and approximately 150°. Beams of the linear image formed on the front face of the inspection substrate 1 by the cylindrical lens 5 are nearly parallel in the vicinity of the front face of the inspection substrate 1 in a direction perpendicular to the linear image. A width w of the parallel beams in the vicinity of the front face of the inspection substrate 1, which is a distance in a direction perpendicular to the inspection surface of the inspection substrate 1, is set to be 9 $\mu$m according to a calculation expression EX below based on the condition that the angle of incidence $\alpha$ is 2°, the photodetecting angle $\alpha$ is 150°, a refractive index n of the inspection substrate to the air is 1.5, and a thickness t of the inspection substrate is 700 $\mu$m:

$$w < 2 * \sin \alpha * t \{\tan[\sin^{-1}\{\sin(90°-\alpha)/n\}] - \tan[\sin^{-1}\{\sin(\theta-90°)/n\}]\} \quad \text{EX}$$

The foreign substance inspecting method of the embodiment constituted as above operates in the following manner.

Figure 8:
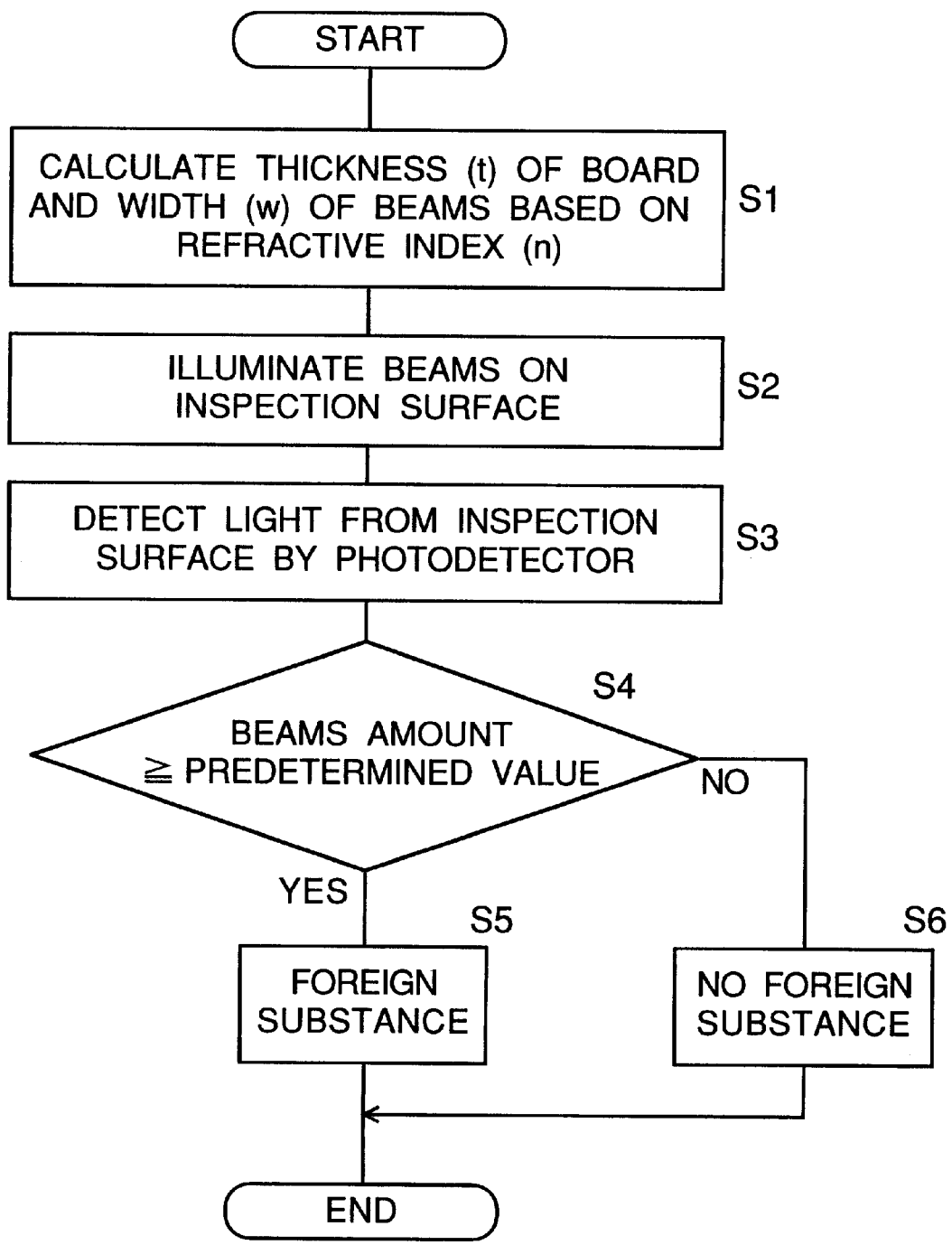
FIG. 8 is a flow chart showing the foreign substance inspecting method carried out by the foreign substance inspecting apparatus according to the first embodiment.

A linear area on the front face of the inspection substrate 1 is illuminated by the beams forming the linear image through the laser light source 2, collimator lens 3, and cylindrical lens 5 in FIG. 1. If a foreign substance 10 exists on the front face in the illuminated area, the beams produce a scattering or reflecting light and a part of the light is condensed by the lens 6, whereby an image is formed on the line sensor 9. The image is photoelectrically converted by the line sensor 9 and judged as the foreign substance by the judging circuit 100. The inspection substrate 1 loaded on the movable table (not shown) is scanned all over the surface in the y main scanning direction which is perpendicular to the beams on the inspection substrate 1 and in the x sub scanning direction. The foreign substance on the whole front face of the inspection substrate 1 is hence inspected. That is, as shown in FIG. 8, at step S1, the thickness t of the substrate (board) and the width w of the beams are calculated based on the refractive index n by a calculating part 101 described later. At step S2, the beams are illuminated on the inspection surface of the inspection substrate 1. At step S3, light from the inspection surface is detected by the line sensor 9 serving as photodetector. At step S4, it is decided by the judging circuit 100 whether or not the amount of beams is not smaller than the predetermined value, i.e. a predetermined threshold value. When the amount of beams is not smaller than the predetermined value, it is decided that there is foreign substance at step S5. When the amount of beams is smaller than the predetermined value, it is decided that there is no foreign substance at step S6.

Figure 5:
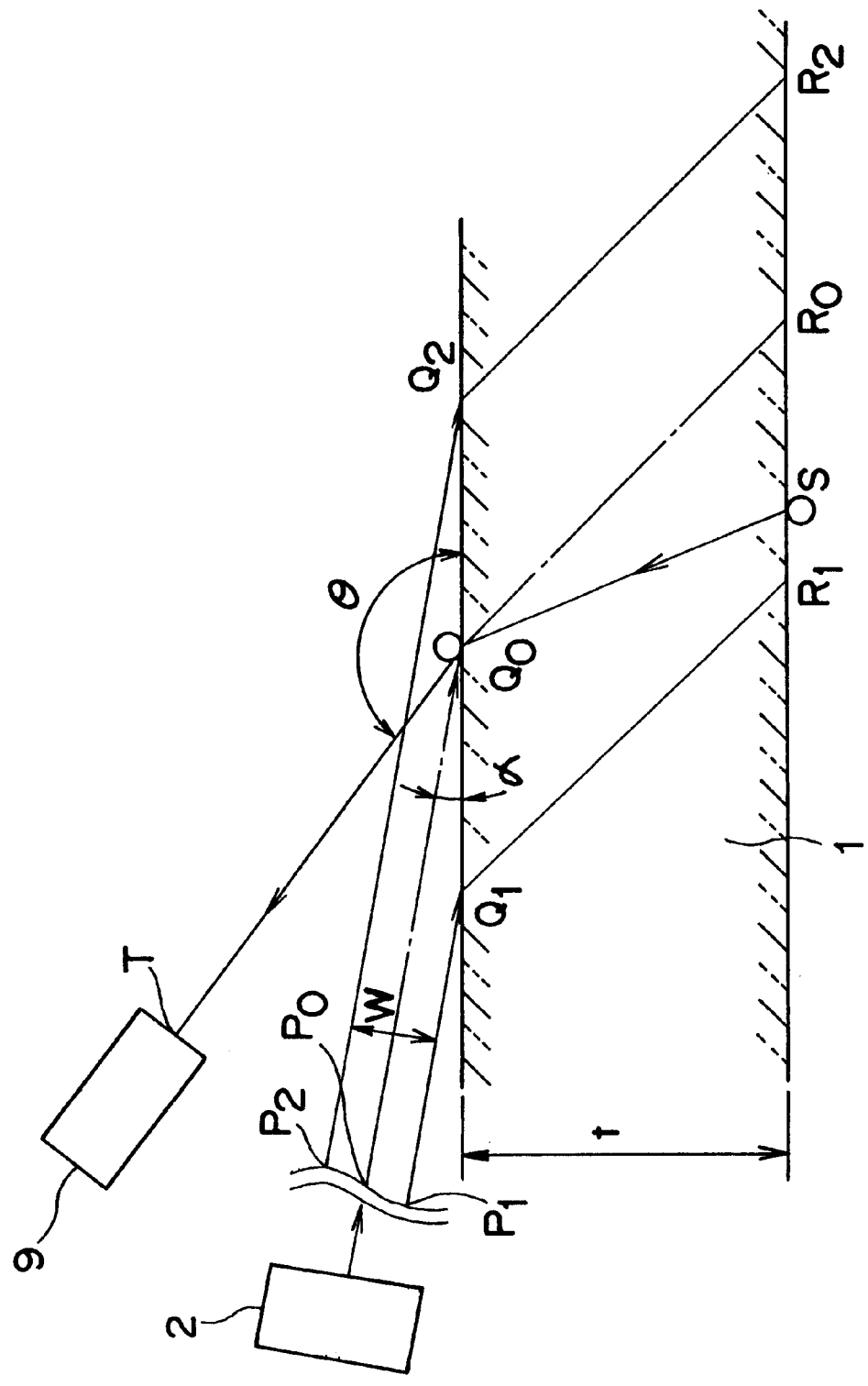
FIG. 5 is a explanatory diagram of conditions for a foreign substance a rear face to be detected.
Figure 6:
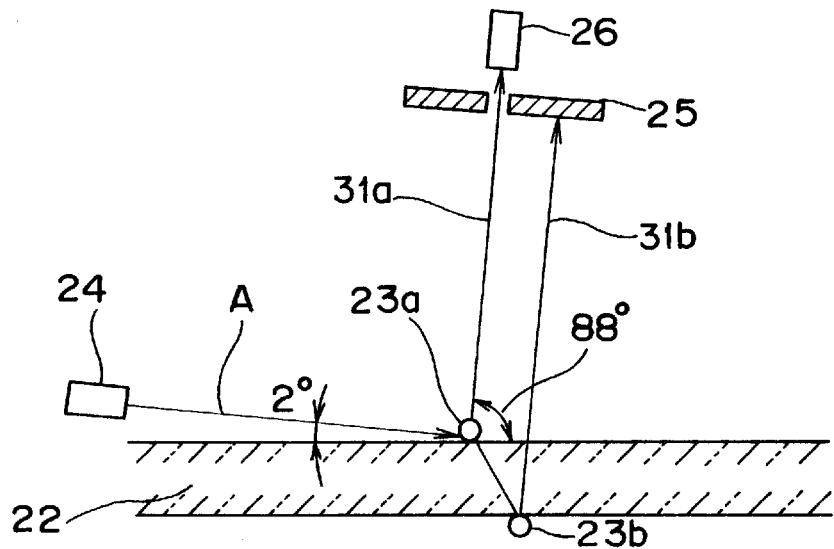
FIG. 6 is a diagram representing the principle of a conventional foreign substance inspecting apparatus.
Figure 7:
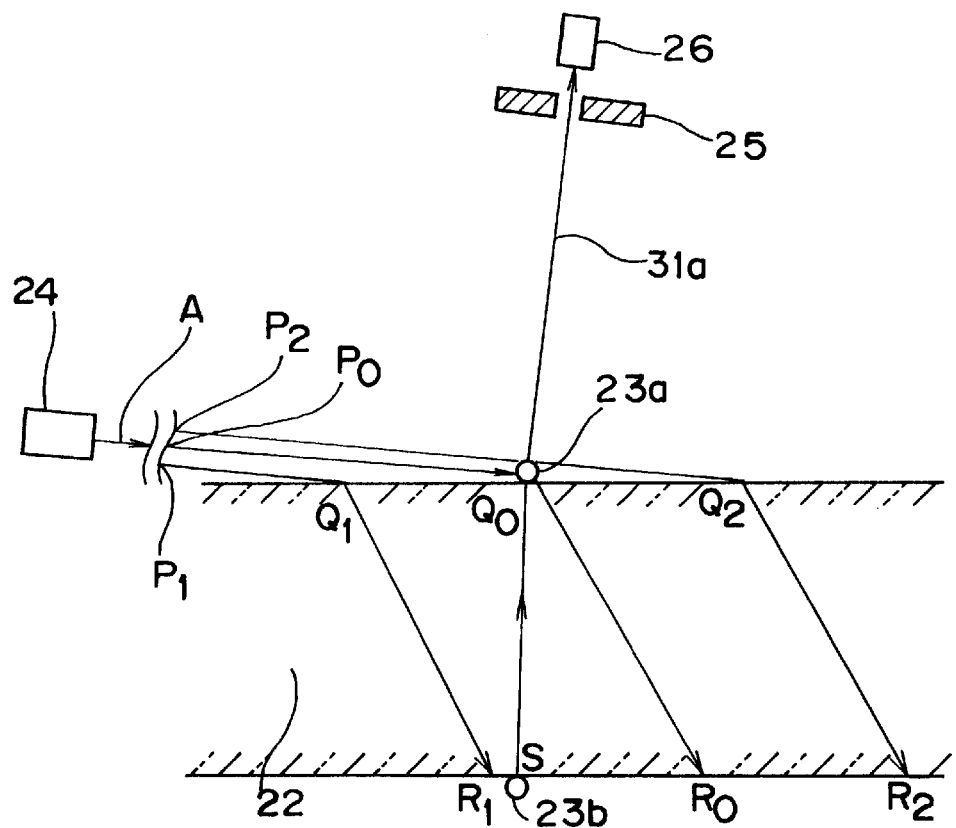
FIG. 7 is a explanatory diagram of conditions when a foreign substance at a rear face is detected in the conventional foreign substance inspecting apparatus.

The reason why the beam width w is found as above according to the calculation expression EX will be described here. In the first place, the reason why a foreign substance at a rear face of the inspection substrate 1 is detected in the case where the beam width w is larger than a predetermined value calculated from the expression EX will be discussed with reference to FIG. 5. A lower end of the beams runs to the front face of the inspection substrate 1 along a route $P_1Q_1$, is refracted, and reaches the rear face of the inspection substrate 1 along a route $Q_1R_1$. An upper end of the beams is brought to the front face of the inspection substrate 1 along a route $P_2Q_2$ finally to the rear face of the inspection substrate 1 along a route $Q_2R_2$ after being refracted at the front face. In this case, if a foreign substance is present in a range $R_1-R_2$ of the rear face, the foreign substance is hit by the beams, whereby the beams are scattered or reflected. Considering a route for the scattering or reflecting light from the foreign substance present at the rear face of the substrate to enter the line sensor 9 serving as a photodetector, a part of the scattering or reflecting light generated from the foreign substance at a position S of FIG. 5 is guided along a route $SQ_0$ to the front face of the inspection substrate 1, and enters the line sensor 9 along a route $Q_0T$ after being refracted. Therefore, if the beam width w is larger than the predetermined value and the beams enter the range $R_1-R_2$ of the rear face of the inspection substrate when the foreign substance exists at a specific position in this range (position S) as shown in FIG. 5, the beams are scattered or reflected and partly brought into the line sensor 9. As a result, although the foreign substance exists at the rear face of the inspection substrate 1, the light is really detected as the foreign substance.

Figure 4:
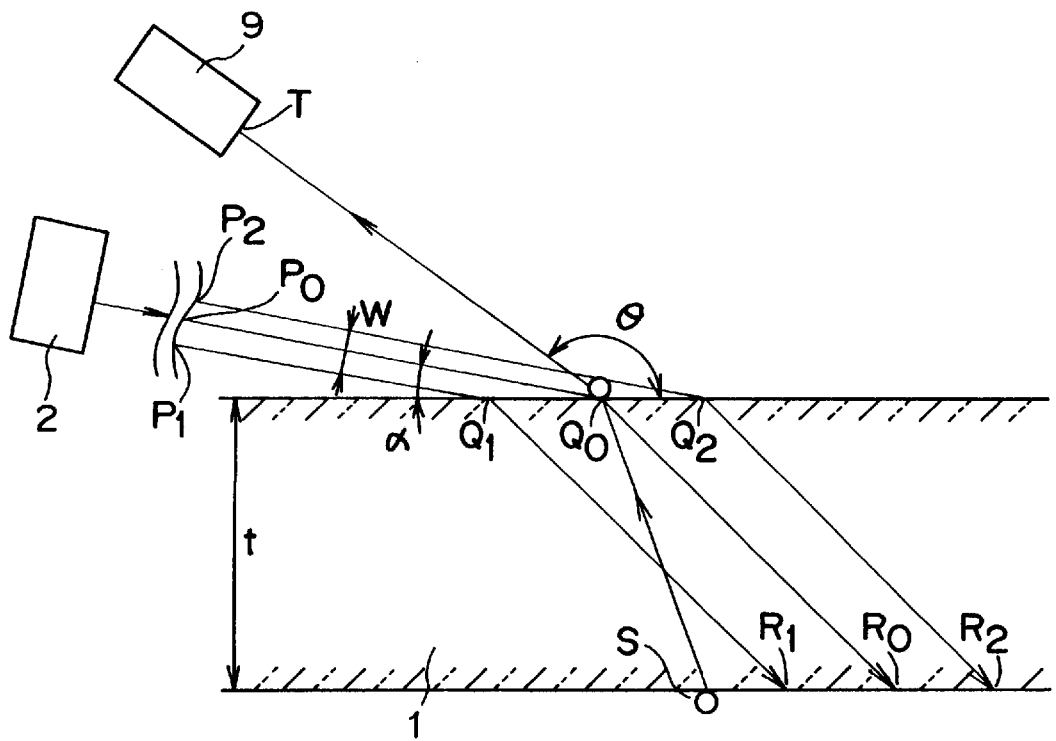
FIG. 4 is a explanatory diagram of conditions for a foreign substance at a rear face not to be detected.

Secondly, the reason why the foreign substance at the rear face of the inspection substrate 1 is prevented from being detected, if the beam width w calculated from the calculation expression EX is smaller than the predetermined value, will be depicted with reference to FIG. 4. Because of the small beam width w, the range $R_1-R_2$ of the rear face of the inspection substrate 1 when the beam reaches is reduced as shown in FIG. 4, and therefore the beams are never guided to the position S from which the beams were incident to the line sensor 9 if the foreign substance were present. Since the light from the foreign substance at the rear face does not reach the line sensor 9, the foreign substance at the rear face of the inspection substrate 1 is not detected at all.

Now, calculation expressions regulating the condition for the beam width w in order not to detect the foreign substance at the rear face will be described with reference to FIG. 3. Supposing that an intersection of the rear face and a perpendicular line from a point $Q_0$ to the rear face is $Q_0'$, an expression (1) below should be held so that the position S is not present in the range $R_1-R_2$:

$$Q_0'S < Q_0'R_1 \quad (1)$$

When $\angle Q_0'Q_0S = \phi$, the following equation (2) is held, in which t is the thickness of the inspection substrate 1:

$$Q_0'S = t * \tan \phi \quad (2)$$

According to the Fresnel's law, the following equation (3) is held when the inspection substrate 1 shows the refractive index n to a substance thereover:

$$\sin \phi / \sin(\phi - 90°) = 1/n \quad (3)$$

An equation (4) is obtained from the equations (2) and (3), as:

$$Q_0'S = t * \tan(\sin^{-1}(\sin(\theta - 90°)/n)) \quad (4)$$

Next, $Q_0'R_1$ will be found. Supposing that an intersection between a perpendicular line from a point $Q_1$ to the rear face of the inspection substrate 1 and the rear face is $Q_1$, $Q_0'R_1$ is as follows:

$$Q_0'R_1 = Q_1'R_1 - Q_1'Q_0' = Q_1'R_1 - Q_1Q_0 \quad (5)$$

The equation (5) becomes an equation (6) when $\angle Q_1'Q_1R_1 = \beta$ is satisfied:

$$Q_1'R_1 = t^* \tan \beta \quad (6)$$

According to the Fresnel's law:

$$\sin(90°-\alpha)^* \sin \beta = n \quad (7)$$

When the beam width is w:

$$Q_1Q_0 = (w/2)/\sin \alpha \quad (8)$$

Accordingly, an equation (9) is obtained from the above equations (5)–(8):

$$Q_0'R_1 = [t^* \tan(\sin^{-1}(\sin(90°-\alpha)/n)) - w]/(2^* \sin \alpha) \quad (9)$$

The condition for setting the width w which is shown in the earlier-described expression EX results from the expressions (1), (4), and (9).

Figure 3:
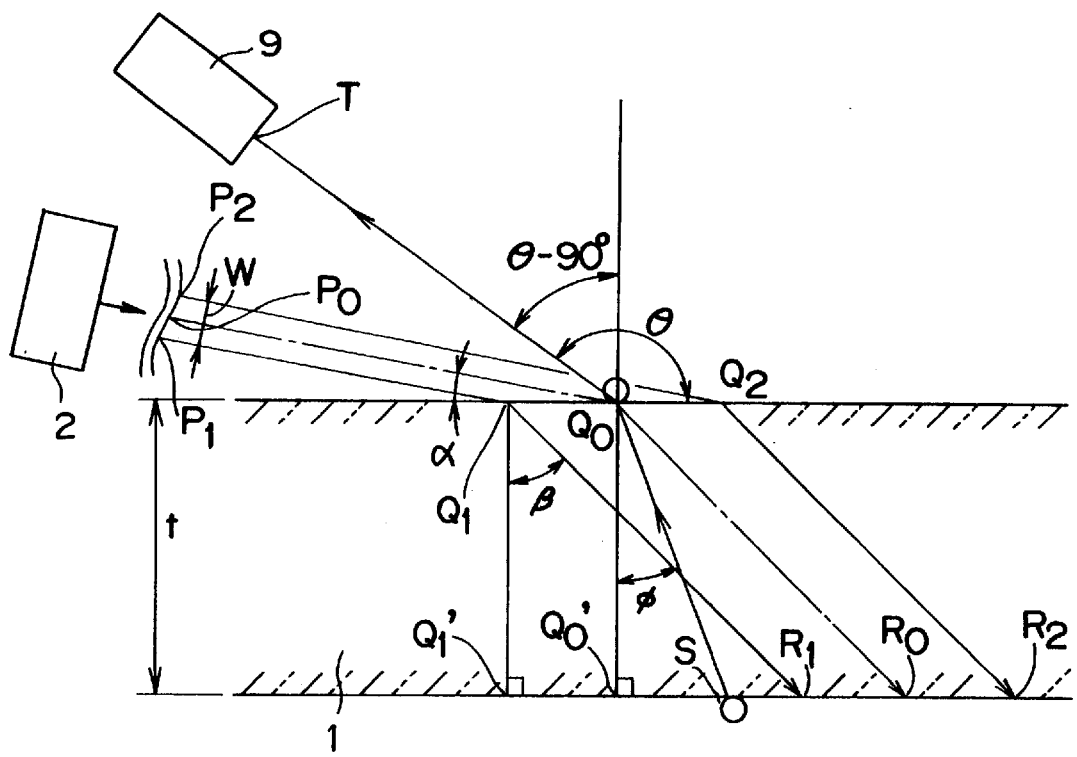
FIG. 3 is a diagram indicative of conditions of a beam width of an illumination in the first embodiment.

The expression EX is related to a case where the photodetecting angle $\theta$ is larger than 90° in FIG. 3. The same applies to a case when the photodetecting angle $\theta$ is not larger than 90°.

The beam width w is specifically determined as follows based on the expression EX in some cases so as not to detect the foreign substance at the rear face of the inspection substrate 1. What is common in the following cases is that the inspection substrate is formed of glass having the thickness t of 700 μm and the refractive index n of 1.5 to a substance thereover, and the illumination light enters with the angle of incidence α of 2°:

1) when $\theta=150°$, $w<9.1$ μm
2) when $\theta=90°$, $w<43.7$ μm
3) when $\theta=30°$, $w<78.2$ μm According to the embodiment, the beam width w is calculated according to the expression EX by a calculating part 101 as described above and is set, by a controller 102 connected to the calculating part 101, as calculated according to the expression EX, so that only the foreign substance adhering to the front face of the light-permeable inspection substrate 1 can be surely detected by the judging circuit 100, in the simple constitution as a whole. The calculating part 101 and controller 102 can serve as a setting unit for setting the width of the beams. The controller 102 also controls the operation of the judging circuit 100 for performing the foreign substances judgement.

The beam width w is a half bandwidth in the vicinity of the focal plane of the inspection substrate 1 when the beams are the laser light from a laser light source. A minimum value of the beam width w is preferably 3–5 μm.

The present invention is not limited to the foregoing embodiment and can be modified in various ways without changing the gist.

For example, the line sensor 9 as the photodetector can be replaced with a photoelectric conversion element such as a photodiode or photomultiplier, etc.

In the embodiment, the beams are reduced to a predetermined width with the use of the cylindrical lens 5 in the illumination part. The predetermined beam width may be achieved by a slit, etc.

The embodiment is based on the assumption that the front face of the inspection substrate 1 undulates or warps a height smaller than the beam width w, and therefore no adjustment mechanism for adjusting a height of the beams in a vertical direction of the substrate is provided. However, if the undulations, warps, or the like of the front face of the inspection substrate 1 are larger than the beam width w, a height measuring means using a laser displacement sensor or the like and a height adjustment mechanism using the measuring result of the sensor should be arranged in the apparatus.

In the above-described constitution of the present invention, the beam width of the illumination light for inspecting foreign substances is set to be w determined according to the calculation expression EX. Therefore, only the foreign substance at the front face of the light-permeable inspection substrate can be detected surely in the simple constitution.

The entire disclosure of Japanese Patent Application No. 8-319838 filed on Nov. 29, 1996, including specification, the claims, drawings, and summary are incorporated herein by reference in its entirety.

Although the present invention has been fully described in connection with the preferred embodiments thereof with reference to the accompanying drawings, it is to be noted that various changes and modifications are apparent to those skilled in the art. Such changes and modifications are to be understood as being included within the scope of the present invention as defined by the appended claims unless they depart therefrom.

What is claimed is:

1. An inspecting method for inspecting particles, which comprises:

projecting beams from an illumination system, arranged above a light-permeable body to be inspected with an angle of incidence of a first elevation angle, onto an upper face of the body;

receiving a reflecting light and a scattering light generated by the beams with a photodetecting angle of a second elevation angle by using a photodetecting system;

calculating a result of an expression $w<2^* \sin \alpha^* t\{\tan[\sin^{-1}\{\sin(90°-\alpha)/n\}] - \tan[\sin^{-1}\{\sin(\theta-90°)/n\}]\}$, from the angle of incidence α which is approximately 2°, the photodetecting angle θ, a thickness t of the body, and a refractive index n of the body to a particle over the body, in order to obtain w; and setting a width of the beams of the illumination system, before the beams are projected, to be not larger than w calculated according to the aforementioned expression.

2. A particle inspecting method according to claim 1, wherein a light source of the illumination system is a laser light source and the beam width of the illumination system is a half bandwidth at a focal plane of the body.

3. A particle inspecting method according to claim 1, wherein the body is a liquid crystal panel.

4. A particle inspecting method according to claim 1, wherein the body is a base board of an optical storage medium.

5. An inspecting apparatus for inspecting particle, which comprises:

an illumination system, arranged above a light-permeable body to be inspected, for projecting beams with an angle of incidence of a first elevation angle onto an upper face of the body;

a photodetecting system for detecting a reflecting light and a scattering light generated by the beam with a photodetecting angle of a second elevation angle;

a calculating unit for calculating a result of an expression $w<2*\sin\alpha*t\{\tan[\sin^{-1}\{\sin(90°-\alpha)/n\}]-\tan[\sin^{-1}\{\sin(\theta-90°)/n\}]\}$, from the angle of incidence $\alpha$ which is approximately 2°, the photodetecting angle $\theta$, a thickness t of the body, and a refractive index n of the body to a particle over the body, in order to obtain w; and a setting unit for setting a width of the beams of said illumination system to be w calculated according to the aforementioned expression.

6. A particle inspecting apparatus according to claim 5, wherein a light source of said illumination system is a laser light source and the beam width of said illumination system is a half bandwidth at a focal plane of the body.

7. A particle inspecting apparatus according to claim 5, wherein the body is a liquid crystal panel.

8. A particle inspecting apparatus according to claim 5, wherein the body is a base board of an optical storage medium.

\* \* \* \* \*